| United States Patent [19] | [11] Patent Number: 4,760,095 |
|---|---|
| Djerassi et al. | [45] Date of Patent: Jul. 26, 1988 |

[54] MOISTURIZERS

[75] Inventors: David Djerassi, New York, N.Y.; Errol S. Schnurman, Rockaway, N.J.

[73] Assignee: Hoffmann-La Roche, Inc., Nutley, N.J.

[21] Appl. No.: 823,214

[22] Filed: Jan. 28, 1986

[51] Int. Cl.$^4$ .................. A61K 7/48; A61K 7/027; A61K 7/06; A61K 7/32

[52] U.S. Cl. .................. 514/847; 424/64; 424/65; 424/70; 514/458; 514/887

[58] Field of Search .................. 424/70, 64, 65; 514/847, 887, 458

[56] References Cited

U.S. PATENT DOCUMENTS

| 4,000,276 | 12/1976 | Hasunuma et al. | 424/251 |
|---|---|---|---|
| 4,216,201 | 8/1982 | Calvo et al. | 424/63 |
| 4,525,344 | 6/1985 | Tutsky | 424/73 |

FOREIGN PATENT DOCUMENTS

| 158090 | 2/1985 | European Pat. Off. | 514/847 |
|---|---|---|---|
| 165457 | 5/1985 | European Pat. Off. | 514/847 |
| 866830 | 7/1949 | Fed. Rep. of Germany | 514/847 |
| 21442499 | 9/1970 | Fed. Rep. of Germany | 514/847 |
| 14932 | 4/1973 | Japan | 514/844 |
| 1239965 | 7/1971 | United Kingdom | 424/47 |

OTHER PUBLICATIONS

Kayano et al, Chem. Abs., 1974, vol. 80, 124592r.
Muyashita et al, Chem. Abs., vol. 80, 1974, 63760r, (Equivalent of 14932).
Chemical Abstracts, vol. 99, No. 1, Jul. 4, 1983, Abstract of Jap. Patent Pub. (Kokai) No. 193, 472/82.
Patent Abstracts of Japan, 2, No. 59, 393 C 78 (1978), Abstract of Japan Patent Pub. (Kokai) No. 15429/78.
Austria–Codex–Drug Information–1984/1985, p. 362 "Mamellin–Salbe".

Primary Examiner—Dale R. Ore
Attorney, Agent, or Firm—Jon S. Saxe; George M. Gould; William H. Epstein

[57] ABSTRACT

Fatty acid esters of α-tocopherol and mixtures thereof which provide a moisturizing composition for topical application and their use in cosmetic preparations.

7 Claims, No Drawings

MOISTURIZERS

SUMMARY OF INVENTION

In accordance with this invention, it has been discovered that when a fatty acid ester of alpha-tocopherol or compositions containing mixtures of these fatty acid esters are topically applied to skin, they provide a moisturizing effect on the skin which can be sustainable for at least 15 hours and in some cases for over 24 hours. These fatty acid esters can be incorporated into cosmetic compositions in conjunction with cosmetically active materials to impart this beneficial moisturizing effect to these compositions. On the other hand, these fatty acid esters can be utilized by themselves in conjunction with cosmetically acceptable organic solvents to moisturize the skin for the above long periods of time.

The compositions of this invention not only moisturize but also provide firmness, elasticity, smoothness and softness to the skin. In addition, after prolonged application of the compositions of this invention, the skin is visibly retexturized.

DETAILED DESCRIPTION

The alpha-tocopherol esters of this invention have the formula:

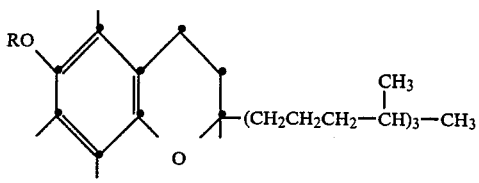

wherein R is a 14 to 22 carbon atom residue of a fatty acid after removal of the OH group.

As used herein, the term "fatty acid" designates an saturated or unsaturated aliphatic monocarboxylic acid containing from 14 to 22 carbon atoms where the unsaturated monocarboxylic acids contain from 1 to 3 double bonds, preferably 1 or 2 double bond. Among the preferred fatty acids are linoleic acid, stearic acid, palmitic acid, oleic acid, linolenic acid, myristic acid, etc.

The term "lower alkyl" as used throughout this application designates a monovalent saturated aliphatic hydrocarbon containing from 1 to 7 carbon atoms such as methyl, ethyl, propyl, isopropyl, n-propyl, etc.

In accordance with this invention, the fatty acid ester of α-tocopherol as defined herein can be utilized either as a moisturizer component in cosmetic composition containing a cosmetically active component or by itself as a moisturizer in a moisturizing topical composition. Generally, it is preferred that the moisturizing component either in the topical cosmetic composition or in the moisturizing composition be a mixture of these fatty acid esters of α-tocopherol. The moisturizing component when applied to human skin imparts a moisturizing effect to the skin which can last for at least 15 hours or longer. By application of the moisturizing component, either by itself or to enhance cosmetic preparations, the skin is rendered measurably firmer with more elasticity having a smoother and softer touch and look. After extended application, the skin is visibly retexturized.

The moisturizing component can be utilized in conventional cosmetic composition to enhance the moisturizing effect of these compositions. These cosmetic compositions contain a cosmetically active ingredient which is topically administered to human skin to provide a cosmetic effect. Among the conventional cosmetically active material into which this moisturizing component can be utilized are included surfactants, emollients, colorants, conditioners, bacteriocides, astringents, detergents, etc. In accordance with this invention, the moisturizing component can be utilized in any conventional cosmetic composition for topical application. Among the preferred type of topical cosmetic preparations or compositions are included creams, lotions, lipsticks, lip balms, chapsticks, shampoos, conditioners, deodorants, hair care products, powders, soaps, etc.

In addition to the cosmetically active ingredients, these moisturizing or cosmetic compositions can contain any of the conventional excipients and additives commonly used in preparing topical cosmetic compositions. Among the conventional additives or excipients which can be utilized in preparing these cosmetic compositions in accordance with this invention are preservatives, thickners, perfumes and the like which are recognized as being conventional in the art of cosmetic compounding. In addition, conventional anti-oxidants such as butylated hydroxyanisole (BHA), butylated hydroxytoluene (BHT), ethoxyquin and the like can be incorporated into these compositions.

The cosmetic composition can contain the conventional cosmetically acceptable carriers for topical application which are generally utilized in the art. These compositions may also contain thickening agents, humuectants, emulsifying agents and viscosity stabilizers such as generally utilized in the art. In addition, these compositions can contain flavoring agents, colorants, and perfumes, which are conventional in preparing cosmetic compositions.

In formulating these cosmetic compositions containing a cosmetically active substance or material which had enhanced moisturizing effect due to the presence of the moisturizing component of this invention, generally the moisturizing component is present in an amount of from about 0.1% to 15% by weight of the total weight of this composition depending upon the degree of moisture enhancement to be provided. If amounts lower than 0.1% are utilized, very little moisturizing effect will be imparted to the composition. Amounts greater than 15% by weight of the moisturizing component can be utilized. However, such large amounts generally do not add any substantial enhancement to the cosmetic compositions over and above that provided by 15% by weight of the moisturizing component. In general, the preferred cosmetic compositions containing from about 1% to about 5% by weight of the moisturizing component. The cosmetically active material can be present in any amount in the composition to impart the cosmetic effect to the skin.

The moisturizing component utilized in accordance with this invention can be the fatty acid ester of α-tocopherol itself such as the linoleic acid ester of α-tocopherol, the oleic acid ester of α-tocopherol, the linolenic acid ester of α-tocopherol, the palmitic acid of α-tocopherol, the stearic acid ester of α-tocopherol, the myristic acid ester of α-tocopherol, each as an individual component or as mixtures of two or more of the above components. Generally, it is preferred to provide a mixture of these fatty acid esters of α-tocopherol as the moisturizing component.

In accordance with the preferred embodiment of this invention, we have found that new and unexpected moisturizing results are produced through the use of a mixture of fatty acid esters of α-tocopherol and particularly a mixture of fatty acid esters where the mixture contains by weight of the total mixture of fatty acid esters of α-tocopherol the following weight percent of esters.

TABLE 1

| Fatty Acid Esters Of Alpha Tocopherol | % By Weight |
|---|---|
| Linoleic Acid | 30% to 70% |
| Oleic Acid | 15% to 40% |
| Linolenic Acid | 2% to 30% |
| Palmitic Acid | 0.5% to 20% |
| Myristic Acid | 0.1% to 10% |
| Stearic Acid | 0.1% to 10% |

In these mixtures, generally 40% to 60% by weight of the total mixture of linoleic acid and 20% to 30% by weight of the total mixture of oleic acid are preferred. Generally, mixtures of the fatty acid esters of α-tocopherol provide little, if any, irritation to human skin when applied topically.

In accordance with this invention, we have found that a composition having the specific fatty acid ester content given above provides an increased moisturizing effect when incorporated into a cosmetic preparation containing a cosmetically active material or when utilized by itself in combination with organic solvent carriers which are cosmetically acceptable.

In utilizing the fatty acid esters of α-tocopherol or any mixture thereof as a moisturizer in a moisturizing composition or by itself in combination with a cosmetically acceptable organic solvent as the carrier, any of the fatty acids of α-tocopherol as defined above or any of the mixtures thereof can be utilized. Generally, it is preferred to utilize the mixtures set forth in Table 1 above in these moisturizing compositions. In a moisturizing composition, it is generally preferred to utilize, about 30% to 75% of the moisturizing component which can be any fatty acid ester of α-tocopherol or its mixtures thereof, including the mixture set forth in Table 1 in a cosmetically acceptable organic carrier. In formulating these moisturizing compositions, the moisturizing component is usually dissolved or emulsified in a cosmetically acceptable organic solvent. Any conventional cosmetically acceptable organic solvent can be utilized in formulating this moisturizing composition. Among the preferred organic solvents are oils such as mineral oil, lower alkyl esters of fatty acids and the alcohols such as methyl, ethyl or isopropyl alcohol. These compositions can contain any of the conventional excipients such as stabilizers, perfumes, emulsifying agents, preservatives, etc. On the other hand, the organic solvent can comprise the rest of the composition, depending upon the type of composition desired to be formulated.

The invention is illustrated by the following examples. In Example 1, the fatty acid mixture utilized has the following composition:

| Fatty Acid | % By Weight of Fatty Acid |
|---|---|
| Linoleic Acid | 65.5% |
| Oleic Acid | 19.5% |
| Linolenic Acid | 10.5% |
| Palmitic Acid | 3.5 |

| Fatty Acid | % By Weight of Fatty Acid |
|---|---|
| Myristic Acid | 0.5% |
| Stearic Acid | 0.5% |

EXAMPLE 1

Preparation of α-Tocopherol Fatty Acid Esters

| | |
|---|---|
| | A 5.0 L three-necked, round-bottomed flask, equipped with a thermometer, a dropping funnel, a condenser, a mechanical stirrer and a scrubber was charged with |
| 646 gm | (2.29 moles) of the fatty acid mixture and |
| 2.0 L | of toluene. The light yellow solution was warmed on a steam bath to 45° C. while |
| 400 gm | (3.36 moles) of thionyl chloride was added over 15 minutes. The solution was stirred an additional 3 hours at 90° C. The excess thionyl chloride was then removed by distillation at 26–28 mm Hg and 50° C. The residual dark oil was triturated with 2 × 500 cc = |
| 1.5 L | of hexane. The hexane mixture was concentrated to an oil after each trituration to give 687 g (2.29 moles) of the acid chlorides of the above fatty acid mixture. At this point a second 5.0 L three-necked round-bottomed flask was charged with |
| 984 gm | (2.28 moles) of α-tocopherol, |
| 1.4 L | of methylene chloride and |
| 734 mL | of pyridine. The resulting solution was stirred at room temperature and |
| 687 gm | (2.29 moles) of the above acid chlorides dissolved in |
| 1.0 L | of methylene chloride was added over a 20-minute period. The reaction exhibited an exotherm to 54° C. The mixture was stirred for 3 hours and then was quenched by adding into a stirred mixture of |
| 2.0 L | water and |
| 2.0 L | of methylene chloride. The organic layer was washed with 2 × 1.0 L = |
| 2.0 L | of 3N hydrochloric acid followed by |
| 2.0 L | of saturated brine. The organic layer was concentrated at 26–28 mm Hg on a rotary evaporator at 50° C. to give 1.58 kg of crude mixture of fatty acids esters of α-tocopherol (crude ester mixture) as a dark viscous oil. The crude ester mixture was purified using |
| 3.4 kg | of silica qel 400 mesh loaded onto a large sintered glass funnel. This recycled plug of silica gel was charged with |
| 1.58 kg | of crude ester mixture dissolved in |
| 1.5 L | of hexane. The silica gel plug was then eluted with |
| 15.0 L | of 10% by volume diethyl ether 90% by volume hexane into five side arm flasks under a 70 mm vacuum. |

| Fraction | Amount Collected | Quality |
|---|---|---|
| 1 | 1.0 L | Pure Ester Mixture |
| 2 | 3.5 L | Pure Ester Mixture |
| 3 | 3.5 L | Ester Mixture and Linoleic Acid |
| 4 | 3.5 L | Linoleic Acid & Imp. |
| 5 | 3.5 L | Linoleic Acid & Imp. |

Fractions #1 and 2 were combined and concentrated at 26–28 mm Hg (55° C.) to give 1.0 kg of the mixed fatty acid esters of α-tocopherol as a light amber oil. Fraction #3 was concentrated to a dark oil at 26–28 mm Hg (55° C.) to give 395 g of low grade ester mixture. The 395 g of crude ester mixture of Fraction

| | -continued |
|---|---|
| 500 mL | 3 was dissolved in of hexane and placed on a fresh plug of |
| 500 gm | silica gel 60 (230–400 mesh). The column was eluted with |
| 2.0 L | of hexane. The eluant was concentrated at 26–28 mm Hg (55° C.) to give 310 g of the mixture of fatty acid esters of α-tocopherol as a light amber oil. All of the fractions were combined at placed under a 0.5 mm Hg vacuum at 70° C. for 3 hours, to give 1.244 kg (1.79 moles) of a pure fatty acid ester mixture of α-tocopherol as a viscous amber oil (78% overall yield). Upon analysis, this mixture contained the following components: 50.5% by weight of the mixture of α-tocopherol linoleate 29.5% by weight of the mixture of α-tocopherol oleate 20% by weight of a mixture of α-tocopherol linolenate; α-tocopherol palmitate α-tocopherol myristate and α-tocopherol stearate. |

This purified fatty acid ester mixture is used in the compositions set forth in the subsequent Examples.

EXAMPLE 2

Lipstick

| Ingredients | % By Weight |
|---|---|
| Vitamin E. Fatty Esters of Example 1 | 3% |
| Candelilla Wax | 11.5% |
| Beeswax | 9.0% |
| Cetyl Alcohol | 5.0% |
| Petrolatum | 15.0% |
| Butyl Stearate | 5.0% |
| D & C Red No. 21 | 1% |
| D & C Red No. 19, Barium Lake | 4.5% |
| D & C Red No. 11, Calcium Lake | 2.5% |
| Rose Oil | 0.5% |
| Castor Oil | q.s. to 100.0% |

EXAMPLE 3

Moisturizing Lotion

| Ingredients | % By Weight |
|---|---|
| Vitamin E. Fatty Esters of Example 1 | 5% |
| Stearic Acid | 4.0% |
| Glyceryl Stearate (and) Polyethylene Glycol-100 Stearate | 4.0% |
| Isopropyl Palmitate | 1.0% |
| Mineral Oil | 1.0% |
| Propylparaben | 0.1% |
| Methylparaben | 0.15% |
| Propylene Glycol | 3.0% |
| Water | q.s. to 100.0% |

EXAMPLE 4

Hair Conditioner

| Ingredients | % By Weight |
|---|---|
| Vitamin E. Fatty Esters of Example 1 | 1% |
| Stearyl Dimethyl Benzyl Ammonium Chloride (Stearalkonium Chloride) | 5% |
| Hydroxypropyl Methylcellulose | 1.5% |

| Ingredients | % By Weight |
|---|---|
| Cetyl Alcohol | 1.5% |
| Water | q.s. to 100.0% |

EXAMPLE 5

Conditioning Shampoo

| Ingredients | % By Weight |
|---|---|
| Vitamin E. Fatty Esters of Example 1 | 0.75% |
| Ammonium Lauryl Sulfate | 25.0% |
| Cocoamidopropyl Betaine | 5.0% |
| Mixture of ethanolamides of Lauric Acid (Lauramide DEA) | 2.0% |
| Propylparaben | 0.05% |
| Methylparaben | 0.20% |
| Water | q.s. to 100.0% |

EXAMPLE 6

Lip Balm

| Ingredients | % By Weight |
|---|---|
| Vitamin E. Fatty Esters of Example 1 | 3% |
| Lanolin Oil | 8.2% |
| Beeswax | 30.0% |
| Ester of Oleic acid and a glycerin polymer (Polyglyceryl 4-Oleate) | 2.0% |
| Paraffin | 15.0% |
| BHT | 0.06% |
| Fructose | 2.0% |
| Mixture of laurate esters of sorbitol and Sorbitol anhydrides (Polysorbate 20) | 2.0% |
| Water | 10.0% |
| Panthenol | 0.1% |
| Glycerin | 2.0% |
| Strawberry Flavor | 0.1% |
| Mineral Oil | q.s. to 100.0% |

EXAMPLE 7

Moisturizing Cream

| Ingredients | % By Weight |
|---|---|
| Vitamin E. Fatty Esters | 4.0% |
| Stearic Acid | 2.2% |
| Polyethylene glycol ether of Oleyl Alcohol | 1.0% |
| Glyceryl Monostearate | 3.5% |
| Isopropyl Palmitate | 5.0% |
| Polyethylene glycol ether of Lanolin Alcohol | 1.0% |
| Beeswax | 1.5% |
| Propylparaben | 0.1% |
| Triethanolamine | 1.0% |
| Propylene Glycol | 3.0% |
| Water | 50.0% |
| Methylparaben | 0.1% |
| Mineral Oil | q.s. to 100.0% |

EXAMPLE 8

Body/Face Oil

| Ingredients | % By Weight |
|---|---|
| Vitamin E. Fatty Esters | 70% |
| Isopropyl Palmitate | 30% |

We claim:

1. In a cosmetic composition for topical application to skin containing a moisturizer present in said composition in an amount sufficient to impart a moisturizing effect wherein the improvement comprises said moisturizer containing from about 30% to 70% by weight of said moisturizer of the linoleic acid ester of α-tocopherol and 15% to 40% by weight of said moisturizer of the oleic acid ester of α-tocopherol.

2. In the improvement of the cosmetic composition of claim 1, wherein the moisturizer comprises from about 0.1% to 15% by weight of said cosmetic composition.

3. In the improvement of the cosmetic composition of claim 1 wherein the moisturizer contains additional esters of α-tocopherol with linolenic acid, palmitic acid, myristic acid or stearic acid.

4. In the improvement of the cosmetic composition of claim 3 wherein said additional esters are present in the moisturizer in the following amounts: from about 2% to about 30% by weight of said moisturizer of the linolenic acid ester of α-tocopherol, from about 0.5% to 20% by weight of said moisturizer of the palmitic acid ester of α-tocopherol, from about 0.1% to 10%, by weight of said moisturizer, of the stearic acid ester of α-tocopherol, and from about 0.1% to 10% by weight of said moisturizer of the myristic acid ester of α-tocopherol.

5. A moisturizing preparation for imparting moisture to skin, said moisturizing preparation containing from about 30% to 70% by weight of said preparation of the linoleic acid ester of α-tocopherol and from about 15% to 40% by weight of said preparation of the oleic acid ester of α-tocopherol and a cosmetically acceptable carrier.

6. The moisturizer preparation of claim 5 wherein the moisturizer preparation contains additional esters of α-tocopherol with linolenic acid, palmitic acid, myristic acid or stearic acid.

7. The moisturizer preparation of claim 6 wherein said additional esters of α-tocopherol are present in the moisturizer preparation in the following amounts: from about 2% to 30% by weight of said preparation of the linolenic acid ester of α-tocopherol, from about 0.5% to 20% by weight of said preparation of the palmitic acid ester of α-tocopherol, from about 0.1% to 10% by weight of said preparation of the myristic acid ester of α-tocopherol and from about 0.1% to 10% by weight of said preparation of the stearic acid ester of α-tocopherol.

* * * * *